United States Patent [19]

Glass

[11] Patent Number: 4,844,869
[45] Date of Patent: Jul. 4, 1989

[54] IMMUNOASSAY APPARATUS

[75] Inventor: Thomas R. Glass, Belmont, Mass.

[73] Assignee: ORD, Inc., North Salem, N.H.

[21] Appl. No.: 773,938

[22] Filed: Sep. 9, 1985

[51] Int. Cl.$^4$ ............................................. G01N 21/77
[52] U.S. Cl. ...................................... 422/68; 250/227;
435/808; 422/58; 436/172; 436/527; 436/535;
436/805; 436/807
[58] Field of Search .............................. 422/52, 55–59,
422/68; 436/172, 527, 535, 800, 805, 807, 808;
435/810, 808; 250/227, 365; 356/311, 445

[56] References Cited

U.S. PATENT DOCUMENTS

| | | | |
|---|---|---|---|
| 4,399,099 | 8/1983 | Buckles | 422/58 |
| 4,447,546 | 5/1984 | Hirschfeld | 422/57 |
| 4,543,477 | 9/1985 | Doi et al. | 250/227 |
| 4,558,014 | 12/1985 | Hirschfeld et al. | 422/58 |
| 4,559,299 | 12/1985 | Rotman | 422/68 |

Primary Examiner—Robert J. Hill, Jr.
Attorney, Agent, or Firm—Schiller, Pandiscio & Kusmer

[57] ABSTRACT

An assay apparatus employing total internal reflection of excitation radiation at the interface between an optically conductive rod or fiber and a surrounding liquid phase of lower index of refraction. Immobilized on the surface of the fiber is a component of a complex formed in an immunochemical-type reaction; a fluorophore that can be excited into fluorescence by the excitation radiation is attached to another component of the complex. The fiber is coaxially mounted in cantelivered position within a length of tubing, so that the excitation radiation can be launched into the unsupported end of the fiber and the fluorescent radiation tunneling back into the fiber may be observed at the same fiber end. To insure that the portion of the fiber surface between the unsupported fiber end and the mounted end is in contact with only surrounding liquid phase, one end of the tubing is provided with a covering having an aperture therein through which at least the unsupported end of the fiber extends, the clearance between the internal periphery of the aperture and the fiber being of capillary dimensions so that the meniscus formed at such clearance will retain fluid in the interspace between the fiber and tube.

14 Claims, 1 Drawing Sheet

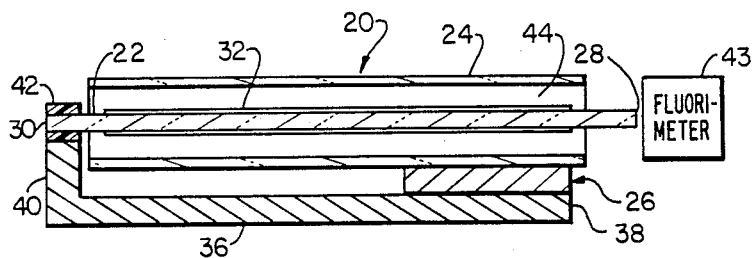
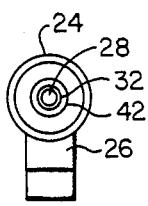
FIG. 1  FIG. 2
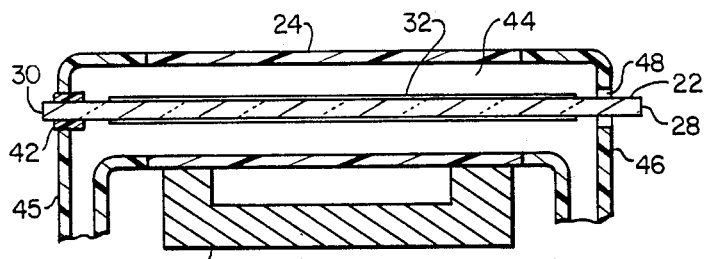
FIG. 4
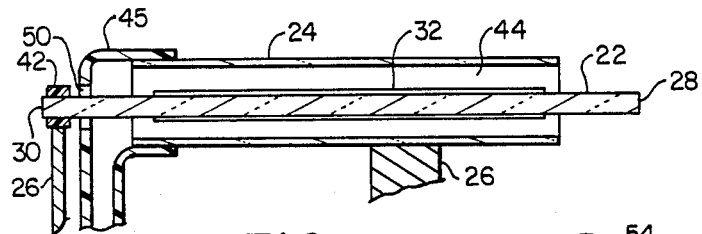
FIG. 5
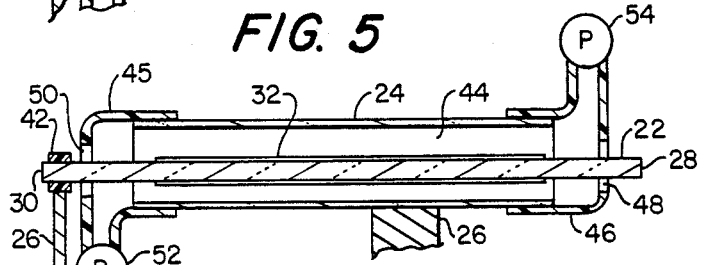
FIG. 3
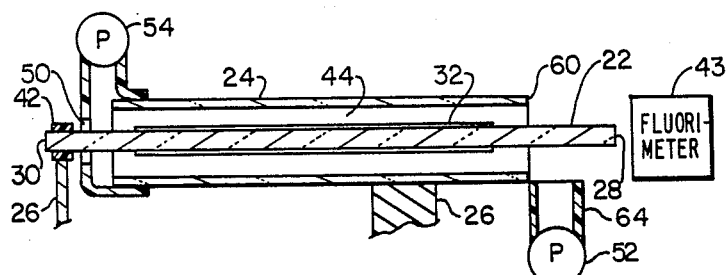
FIG. 6

IMMUNOASSAY APPARATUS

This invention relates to optical apparatus for carrying out chemical and biochemical assays, and more particularly to improved fiber optics apparatus for such assays.

One of the large variety of chemical and biochemical techniques used for analysis or assay, is an optical system employing the principles of attentuated total internal reflection (ATR) spectroscopy. Particularly useful for immunoassays, such an optical system employs an optical wave guide, such as an optical fiber or rod. An antibody is covalently immobilized on a portion of the outer surface of the wave guide, the antibody being reactive with an antigen in a solution to be assayed or tested. A light beam introduced into one end of the wave guide will be totally internally reflected in the dense medium of the wave guide, and will generate in the rarer medium or test solution an electromagnetic waveform, known as the evanescent wave component. The latter characteristically extends only a fraction of a wavelength across the interface between the wave guide and test solution. This penetration, however, is sufficient to permit substantial optical interaction between the evanescent wave component and the immobilized antibody with which the antigen in the test solution will complex, and only minimally with any bulk solution in which the antigen was present. Such optical interaction then permits one to assay the antigen. A number of such systems using internal total reflection spectroscopy for an assay are known and have been described, for example, in U.S. Pat. Nos. 4,133,639 in which is disclosed a system that measures fluorescence induced by the optical interaction; U.S. Pat. No. 4,050,895 which decribes a system based on absorption of the evanescent wave by the analyte; and U.S. Pat. Nos. 4,321,057 and 4,399,099 both of which disclose systems that detect changes in the radiation transmitted through the fiber; U.S. Pat. No. 4,447,546 which describes a fluorescence immunoassay system; and others.

An immunoassay apparatus developed by T. Hirschfeld (U.S. Pat. No. 4,447,546 issued May 8, 1984) employs total internal reflection at an interface between a solid phase and a fluid phase of lower index of refraction to produce an evanescent wave in the fluid phase. Fluorescence excited by the wave is observed at angles greater than the critical angle, by total reflection within the solid medium. The solid phase is arranged and illuminated to provide multiple total internal reflections at the interface. Typically, the solid phase is in the form of an optical fiber to which is immobilized a component of a complex formed in an immunochemical reaction. A fluorophore is attached to another component of the complex. The fluorescent labeled component may be either the complement to or the analog of the immobilized component, depending upon whether competitive or sandwich assays are to be performed. In the case of competitive assays, the labelled component is typically preloaded to the immobilized component in a controlled concentration.

The fiber and the attached constituent of the assay are immersed in a fluid phase sample and the exciting illumination is injected into an input end of the fiber. The evanescent wave is used to excite fluorescence in the fluid phase, and that fluorescence which tunnels back into the solid phase (propagating in direction greater than the critical angle) is detected at the input end of the fiber.

The observed volume of sample is restricted not only by the rapid decay of the evanescent wave as a function of distance from the interface, but by an equally fast decrease with distance of the efficiency of tunneling, the more distant fluorophores not only being less intensely excited and thus fluorescing less, but their radiation is less efficently coupled into the fiber. Consequently the effective depth of the sensed layer is much reduced compared to the zone observed by total reflection fluorescence alone, the coupling efficiency effectively scaling down the zone.

Multiple total internal reflections in the solid phase allow the illuminating beam to excite repeatedly an evanescent wave, thereby more efficiently coupling the small exciation source to the sample volume. This also increases the amount of sample sensed. The latter is also enhanced by diffusive circulation of the sample past the fiber surface and to which the material being assayed adheres by reaction as it passes. Diffusion makes the actually sampled layer thickness much larger than the thin surface layer that is all that contributes to the background.

All of the radiation that tunnels back into the fiber is within the total reflection angle, and is thus trapped within the fiber. The power available from the fluorescence increases with the length of fiber within the fluorescing material. However, the optical throughput of the system (determined by the aperture and the numerical aperture of the fiber) remains constant. The total fluorescent signal coming from the entire surface of the fiber, multiplied by the increase in sample volume due to diffusion, thus becomes available in a very bright spot (that is the cross-section of the fiber in diameter) exiting the fiber at its input end through a restricted angle determined by the critical angle of reflection within the fiber. Such signal is easily collected at high efficiency and throughput matched to a small detector.

For excitation radiation initially propagating through an optical fiber of refractive index $n_0$, otherwise surrounded by a material of refractive index $n_1$, the maximum acceptance angle B of input radiation into the fiber can be found from the equation:

$$NA = n_2 \sin B = (n_0^2 - n_1^2)^{\frac{1}{2}} \tag{1}$$

where $n_2$ is the refractive index of the medium (typically air) through which the radiation is initially propagated so as to be incident upon an end of the fiber, and NA is the so-called numerical aperture of the fiber. Thus, the numerical aperture for a fiber is highest when the fiber core material has a very high index and the medium surrounding it has a very low index, or $n_0 > n_1$. For example, satisfactory sensitivities can be obtained where a glass fiber of ordinary index of refraction is surrounded by an aqueous solution that typically has an index of refraction in the vicinity of 1.33–1.35.

It has been customary to provide means for mounting the fiber so that at least that end of the fiber into which radiation is projected, will be accurately positioned. Contact between the fiber and the mounting means, usually at or adjacent the input end of the fiber, tends to reduce the numerical aperture inasmuch as the refractive index of the mounting material is generally higher than $n_1$. To alleviate this problem, typically the fiber is coated, at least near the end of the fiber into which radiation is propagated, with a cladding, typically of a transparent, high-molecular weight polymer disposed to provide an interposed, low-refractive index medium between the mounting and the fiber. The portion of the fiber intended to contact the analyte solution or sample to be assayed has no such cladding. Ideally, if the index of the cladding is the same as the index of the sample, maximum excitation can be delivered to the sample. Unfortunately, the refractive index of most cladding obtainable is around 1.40 to 1.43, and such indices limit the maximum numerical aperture to a value much lower than the one that might be obtained if a lower index cladding were available.

The evanescent zone tends to increase in depth and the sensitivity of the system also increases as the numerical aperture of the fiber increases. Thus, it is preferred that the numerical aperture of the system be maximized. Such maximization has heretofore been limited by the above-noted impediments imposed by the mounting of the fiber at or near its proximal (i.e. with respect to the input excitation radiation) end.

A principal object of the present invention is therefore to provide an improved assay system employing fiber optics, which system has an improved numerical aperture and thus an increased sensitivity. Other objects of the present invention are to provide such a system that permits direct matching to the numerical aperture of the fiber in a fluid sample; and to provide such a system in which the numerical aperture of the system is maximized, i.e. is substantially as high as is allowed by the refractive indices of the fiber and the fluid sample in contact therewith.

The foregoing and other objects of the present invention are achieved simply by mounting the fiber at or adjacent its distal end and spaced within an enclosure so that the only material in contact elsewhere with the fiber, is the sample. One end of the enclosure is covered with a first elbow having an aperture therein through which the fiber protrudes without contacting the elbow, means being provided for introducing a flow of fluid through the elbow and into the interspace between the enclosure and fiber. Fluorescence is preferably collected from the same end of the fiber through which excitation radiation was injected, so light losses introduced by mounting means at the distal end can be neglected insofar as measurement of the fluorescence is concerned, thereby enabling maximum choice of methods and materials for mounting the fiber.

Other objects of the present invention will in part be obvious and will in part appear hereinafter.

The invention accordingly comprises the apparatus possessing the construction, combination of elements and arrangement of parts, and the method comprising the several steps and relation and order of one or more of such steps with respect to the others, all of which are exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings in which like numerals in the several drawings are employed to denote like parts, and wherein:

FIG. 1 shows, in idealized, enlarged, longitudinal cross-section, an assay device incorporating a fiber optic system and embodying the principles of the present invention;

FIG. 2 is an end elevational view of the assay device of FIG. 1;

FIG. 3 illustrates, in idealized, enlarged longitudinal cross-section, partly in fragment, another assay device incorporating a fiber optic system and embodying the principles of the present invention;

FIG. 4 is a cross-section, partly in fragment, illustrating another version of the assay system of the present invention;

FIG. 5 is a cross-section showing yet another alternative form of the present invention; and FIG. 6 shows still another alternative form of an assay system embodying the principles of the present invention.

Referring to FIGS. 1 and 2, there is shown exemplary apparatus 20 for assaying a fluid sample, which apparatus incorporates the principles of the present invention. Apparatus 20 includes optical fiber 22, hollow, elongated enclosure 24, and mounting means 26, and is similar in many respects to the system shown in the aforesaid U.S Pat. No. 4,447,546.

Fiber 22 is an elongated body extending from its proximal end or entrance face 28 to a distal or terminal end 30, fiber 22 preferably having a substantially circular cross-section. At face 28 the fiber surface typically is planar, is disposed normally to the longitudinal axis of the fiber and is preferably highly polished to minimize any blemishes or surface defects that would tend to scatter incident excitation radiation. Alternatively, face 28 of the fiber may be configured in other desired optical shapes to serve, for example as a magnifying or matching optical surface.

In a preferred embodiment in which the fluorescence, induced at the the fiber surface by excitation radiation launched down the fiber, is collected or observed at the same proximal end of the fiber at which the excitation radiation is injected, it is desired to prevent stray radiation from going back down the fiber from face 30 to face 28. Consequently, face 30 may be shaped to spill out light incident thereon internally, but preferably is coated with a material matching the index of refraction of the medium surrounding face 30, such material being both non-fluorescent and aborbent with respect to the excitation radiation. Typically, an epoxy resin loaded with carbon black serves such function.

Fiber 22 is adapted to propagate along its length, by multiple total internal relection, optical excitation radiation entering entrance face 28 within a conical acceptance angle (B) substantially symmetric with the long axis of the fiber and defined hereinbefore, as well known to those skilled in the fiber optics art, in equation (1). Fiber 22 may be any of a very large number of substantially homogeneously materials optically transparent to the excitation radiation, e.g. glassy materials such as glass, crystalline materials such as quartz, sapphire and the like; synthetic polymers such as polyolefins, polypropylenes and the like, and is preferably quite stiff. Where fiber 22 is to be used in fluid assays as described hereinafter, the index of refraction ($n_0$) of the material forming fiber 22 must be greater than $n_1$, the index of refraction of the fluid being assayed. The latter index is typically about 1.3 for an aqueous solution. For purposes of an immunoassay apparatus, fiber 22 may be as short as 5 mm and typically will have a diameter in the range of from about 1 mm to a few hundred microns, it being understood however, that such length and diameter are merely exemplary and not limiting. The combination of fiber length, diameter and modulus should be selected such that the fiber is short enough and/or stiff enough to be self-supporting in a cantilevered mode.

In an exemplary embodiment, it is intended that the operative portion of the fiber surface be defined by the dimensions of an activated region at which the assay is to be performed. To activate the surface of the operative portion of fiber 22, the latter is typically treated to provide coating 32 such as is described in detail in U.S. Pat. No. 4,447,546 and is incorporated herein by reference.

Enclosure 24 is a tube, preferably but not necessarily optically transparent, and formed of a material that is relatively insoluble and chemically non-reactive with the fluid being assayed. Typically enclosure 24 is simply a glass tube having an inside diameter greater than the maximum outside diameter of fiber 22, and preferably dimensioned to delimit a predetermined volume surrounding at least activated coating 32 on fiber 22. In a preferred embodiment, the interspace between the coated surface of fiber 22 and the inside wall of enclosure 24 is of capillary dimensions.

Mounting means 26 is shown simply as cradle 36 having one portion 38 thereof coupled to and supporting enclosure 24, another portion 40 thereof being coupled to and supporting ferrule 42 in which distal end 30 of fiber 22 is firmly mounted. The material out of which ferrule 42 is formed is not important from a standpoint of optics, but should be relatively non-reactive chemically with the fluid sample to be assayed. In the embodiment of FIGS. 1 and 2, enclosure 24 and fiber 22 are shown mounted so that the long axes of both the enclosure and fiber are substantially horizontally with fiber 20 being thus cantilevered to extend internally within enclosure 24 with end 28 protruding outwardly therefrom, fiber 22 being maintained in spaced relation to the internal surface of enclosure 24. In this particular embodiment, enclosure 24 is open at both ends, thereby permitting fluid to be introduced or withdrawn from either end.

In operation of the embodiment of FIG. 1, coating 32 of fiber 22 is formed from any of a number of activating reagents (such as a constituent of an antibody-antigen complex that includes a fluorescent tag) and essentially subjected to the same procedures as are described in U.S. Pat. No. 4,447,546. Briefly, interspace 44 between enclosure 24 and fiber 22 is filled, as with a hypodermic syringe, with a liquid sample of the material to be assayed, the sample being held in interspace 44 by the meniscus surfaces formed at opposite ends of enclosure 24. While in an alternative form of the embodiment of FIG. 1, the end of enclosure 24 adjacent ferrule 30 could be closed over the latter, it would leave only the opposite end of enclosure 24 open, and interspace 44 could not be as conveniently filled and emptied. In either case, the sample is allowed to incubate in interspace 44 as desired to permit the material being assayed in the fluid sample to diffuse to and react with coat 32 to form the tagged complex. The apparatus is coupled to fluorimeter 43 so that entrance face 28 is illuminable with radiation, typically capable of exciting or inducing fluorescence in coat 32 by an evanescent wave accompanying the transmission of the radiation down the fiber. The fluoresence induced in tagged complex at coat 32 then tunnels back into the fiber from the excited material and back out throught face 28 to be read by fluorimeter 43.

The present apparatus permits one to provide an fiber optics assay apparatus with as high a numerical aperture as may be achieved subject to the constraints imposed by the refractive index of the sample and the index of the fiber, inasmuch as there is no degradation in numerical aperture due to a contacting, intervening mounting or cladding material between or at the proximal end of the fiber and that portion of the fiber in which fluorescence is excited. Since one may start with a fairly substantial glass "rod" rather than the fine fibers such as are disclosed in U.S Pat. No. 4,447,546, one is not limited to the type of glass that may be used, i.e. telecommunication glasses, and therefore one may use very high index glasses, crystals, polymers and the like, which further enhances the maximum numerical aperture that can be obtained at the fiber portion in contact with the sample.

It will be appreciated that although the embodiment of FIG. 1 in which the enclosure ends are both open can be used with either a static sample or a sample flow, the alternative embodiment in which the enclosure portion adjacent ferrule 42 is closed is useful substantially only with static samples of fluid. Also, while the embodiment of FIG. 1 has been described as having both the enclosure and fiber disposed horizontally, it it feasible to position them vertically, keeping however in mind that the hydraulic head created thereby should not exceed a force that will overcome the strength of the supporting meniscus at the bottom end of the enclosure.

Referring now to the embodiment shown in FIG. 3, there will be seen another assay apparatus comprising fiber 22, enclosure 24 and mounting 26. Like the embodiment of FIG. 1, mounting 26 of FIG. 3 is coupled to and supports both enclosure 24 and is connected through ferrule 42 adjacent or at distal end 30 of fiber 22. The ends of enclosure 24 are respectively coupled to elbows 45. and 46 typically formed of heat-shrinkable tubing. Elbow 46 is provided with aperture 48 through which proximal end 28 of the fiber extends. Elbow 45 is provided with aperture 50 through which a portion of fiber 22 adjacent distal end 30 extends. Ferrule 42 holds distal end 30 of fiber 22 so as to support fiber 22 in a cantilevered position and to maintain the fiber in a spaced relation inside enclosure 24 and through apertures 48 and 50 so that the fiber does not contact the internal periphery of either aperture. Apertures 48 and 50 are preferably unequal in size.

It will be apparent that the provision of aperture 50 obviates any lateral forces from arising from pressures exerted on the fiber by the elbows, and also that aperture 48 insures that the portion of the fiber extending from ferrule 42 toward proximal end 28 will not contact any material other than the fluid sample. The latter is provided in the form of a flowstream moving in a direction toward distal end 30 where the larger aperture 50 surrounds the fiber, preferably impelled by a pair of pumps 52 and 54 coupled respectively to elbows 45 and 46. Pump 52 coupled to elbow 45 preferably operates in suction, pump 54 operating at positive pressure, thereby maintaining the pressure inside enclosure 24, at least adjacent the apertures, at atmospheric or near atmospheric levels so that ambient atmosphere will not be pulled into aperture 48 or sample liquid forced out of either aperture. To insure that air is taken into the exhaust line defined by elbow 45 preferentially to sample being forced out (keeping in mind that inspired air will only be carried to pump 52 without passing through the enclosure), the flow rate of suction pump 52 is preferably set slightly higher than the flow rate set by supply pump 54.

It is highly desirable that the clearance between fiber 22 and the internal peripheries of apertures 48 and 50 should be of capillary dimensions. This insures that the sample fluid, even when under the pressure required to achieve flow through interspace 44, will be prevented from flowing out of apertures 48 and 50 by the surface tension of the meniscus formed over that minute clearance around the fibers.

A modification of the embodiment of FIG. 3 is shown in FIG. 4 wherein elbow 45 is coupled to and serves as a mounting for supporting ferrule 42, and mounting means 26 is used to support directly only enclosure 24. Because elbow 45 itself serves to mount the fiber, no aperture is provided in the elbow near the distal end of the fiber. In such case, the fluid flow should be directed through the enclosure toward aperture 48, again to prevent air from being inadvertently drawn through the latter and interfering with the sample flow over the coated fiber.

Yet another modification of the present invention is shown in FIG. 5 in which fiber 22 is cantilevered from ferrule 42 through aperture 50 formed in elbow 45. Ferrule 42 is supported, externally of elbow 45, by support means 26. Unlike the embodiment of FIG. 4, the structure of FIG. 5 includes only one elbow, the opposite end of enclosure 24 being open so that fluid introduced under positive pressure into elbow 45 will traverse the enclosure and run out of the open end of the latter. As in the other embodiments, if interspace 44 is maintained at or near capillary dimensions and the pressure on the sample fluid is reduced so that the fluid no longer is impelled through interspace 44, then the meniscus formed at the open end of enclosure 24 by the fluid will hold the latter in the interspace and permit measurements to be effected thereon. Thus the embodiment of FIG. 5 has the advantage of not requiring a pair of pumps, and can be readily employed with a substantially constant fluid flow, a pulsed fluid flow or a substantially static fluid sample in the interspace.

Occasionally, where the flow rates provided by the two pumps serving the embodiments of FIGS. 3 and 4 are disparate, an air bubble may be pulled into the elbow having the larger aperture therein, and such bubble may, in passing by or over the fiber, impart an undesirable vibration or approximate periodic transverse motion to the unsupported fiber end. This problem is obviated by the structure shown in FIG. 6 which is similar to that shown in FIG. 5 except in one respect. One point on an edge of open end 60 of enclosure 24 is in contact with a point on an edge of open end 62 of capillary tube 64, the respective axes of capillary tube 64 and enclosure 24 being substantially normal to one another. Because the edges of open ends 62 and 60 of capillary tube 64 and enclosure 24 respectively are formed at right angles to the long axes of the tube and enclosure, those edges of open ends 62 and 60 are therefore also normal to one another. Clearly, open end 60 of enclosure 24 constitutes a larger aperture than aperture 50. Hence, when a flow of fluid under positive pressure is applied to the enclosure by pump 54 and suction is applied by pump 52, liquid expressed from open end 60 is drawn into capillary 64 by capillary action and is removed, along with a concurrent air stream, by pump 52. Any bubbles formed in the process do not contact fiber 22.

Since certain changes may be made in the above apparatus without departing from the scope of the invention herein involved, it is intended that all matter contained in the above description or shown in the accompanying drawings shall be interpreted as illustrative and not in a limiting sense.

What is claimed is:

1. In apparatus for assaying a fluid sample and including a totally internally reflecting elongated substrate transmissive to radiation capable of providing an evanescent wave for exciting fluorescence in fluorescent material disposed at least on a portion of the surface of said substrate, said substrate also being transmissive to said fluorescence, and elongated means spaced from said surface of said substrate and constructed and arranged so as to define a hollow elongated enclosure surrounding said surface, and means coupled to one end of said substrate for mounting said substrate in a cantilevered position within said enclosure, the improvement wherein one end of said enclosure is covered with a first elbow having an aperture therein through which said substrate protrudes without contacting said first elbow, said apparatus including means for introducing a flow of fluid through said first elbow and into the interspace between said enclosure and said substrate.

2. In apparatus as defined in claim 1 including means for controlling the rate of said flow of fluid.

3. In apparatus as defined in claim 2 wherein said means for controlling said rate of flow comprises fluid pumping means.

4. In apparatus as defined in claim 1 wherein said substrate is an optical fiber and said enclosure is a tube coaxially spaced apart from and surrounding said fiber, and the unsupported end of said fiber protrudes through said aperture.

5. In apparatus as defined in claim 4 wherein the clearance between said fiber and said aperture is of capillary dimensions.

6. In apparatus as defined in claim 4 wherein the opposite end of said tube is open and said fiber protrudes therethrough.

7. In apparatus as defined in claim 6 including a second tube having an open end, the edges of said open ends being substantially normal to one another with a point on each of said respective edges being in contact with one another.

8. In apparatus as defined in claim 7 including means for applying suction to said second tube to draw fluid away from the open end of the latter.

9. In apparatus as defined in claim 1 wherein the supported end of said substrate protrudes through said aperture.

10. In apparatus as defined in claim 1 including a second elbow covering the other end of said enclosure, said second elbow having an aperture therein through which said substrate protrudes without contacting said second elbow.

11. In apparatus as defined in claim 10 wherein the respective apertures in said first and second elbows are of unequal size.

12. In apparatus as defined in claim 11 wherein the clearances between said fiber and said apertures are of capillary dimensions.

13. In apparatus as defined in claim 10 including first fluid pumping means coupled to said first elbow and second fluid pumping means coupled to said second elbow, said first pumping means being operable to provide said fluid under positive pressure to the respective elbow while said second pumping means provide suction to said second elbow, the aperture in said second elbow being greater in size than the aperture in said first elbow.

14. In apparatus for assaying a fluid sample and including a totally internally reflecting elongated substrate transmissive to radiation capable of providing an evanescent wave for exciting fluorescence in fluorescent material disposed at least on a portion of the surface of said substrate, said substrate also being transmissive to said fluorescence, and elongated means spaced from said surface of said substrate so as to define a hollow elongated enclosure surrounding said surface, and means coupled to one end of said substrate for mounting said substrate in a cantilevered position within said enclosure, the improvement wherein said enclosure being covered at least at one end thereof with a cover having an aperture therein through which the other end of said substrate extends without contacting said cover, the clearance between said substrate and the internal periphery of said aperture being of capillary dimensions.

* * * * *